US006482816B1

(12) United States Patent
Uckun et al.

(10) Patent No.: US 6,482,816 B1
(45) Date of Patent: *Nov. 19, 2002

(54) ORGANIC ARSENIC COMPOUNDS

(75) Inventors: Faith M. Uckun, White Bear Lake, MN (US); Xing-Ping Liu, Minneapolis, MN (US)

(73) Assignee: Parker Hughes Institute, Roseville, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/723,220

(22) Filed: Nov. 27, 2000

Related U.S. Application Data

(63) Continuation of application No. 09/338,680, filed on Jun. 23, 1999, now Pat. No. 6,191,123.
(60) Provisional application No. 60/125,337, filed on Mar. 19, 1999.

(51) Int. Cl.$^7$ ..................... C07C 245/10; A61K 31/285

(52) U.S. Cl. ..................... 514/184; 514/186; 544/226

(58) Field of Search .................. 514/186, 184; 544/226

(56) References Cited

U.S. PATENT DOCUMENTS

| | | | | |
|---|---|---|---|---|
| 5,281,588 A | | 1/1994 | Maes et al. ................ | 514/184 |
| 6,191,123 B1 | * | 2/2001 | Uckun et al. ............... | 514/150 |

FOREIGN PATENT DOCUMENTS

| | | |
|---|---|---|
| SU | 997461 | 11/1982 |
| WO | WO 96/16664 | 6/1996 |

OTHER PUBLICATIONS

Simone, Oncology: Introduction, Cecil Textbook of Medicine, 20th Edition, vol. 1, pp. 1004–1010, 1996.*
Weinstein SM., "Integrating Palliative Care in Oncology", Cancer Control, vol. 8 No. 1 pp. 32–35 (Jan./Feb. 2001).
Greenlee RT et al., "Cancer Statistics 2000", CA–Cancer J. Clin. vol. 50 No. 1 pp. 7–33 (Jan./Feb. 2000).
"Mortality Patterns–United States, 1997" MMWR Morb. Mortal. Wkly. Rep., vol. 48 No. 30 pp. 664–668 (Aug. 6, 1999).
Green JA et al., "Survival and recurrence after concomitant chemotherapy and radiotherapy for cancer of the uterine cervix: a systematic review and meta–analysis", Lancet, vol. 358 No. 9284 pp. 781–786 (Sep. 8, 2001).
Recht A., "Postmastectomy Locoregional Radiotherapy: Is It Here to Stay?", Semin Oncol. vol. 28 No. 3 pp. 245–252 (Jun. 2001).
Calvo AR et al., "Lung Cancer: Therapeutic options for stage IV and recurrent NSCLC", Cancer Treat. Res. vol. 105 pp. 189–227 (2001).

Chen GQ et al., "In vitro studies on cellular and molecular mechanisms of arsenic trioxide ($As_2O_3$)in the treatment of acute promyelocytic leukemia: $As_2O_3$ induces $NB_4$ cell apoptosis with downregulation of Bcl–2 expression and modulation of PML–RAR α/PML proteins", Blood, vol. 88 No. 3 pp. 1052–1061 (Aug. 1, 1996).
Shen ZX et al., "Use of arsenic trioxide ($As_2O_3$)in the treatment of acute promyelocytic leukemia (APL): II. Clinical efficacy and pharmacokinetics in relapsed patients", Blood, vol. 89 No. 9 pp. 3354–3360 (May 1, 1997).
Soignet SL et al., "Complete remission after treatment of acute promyelocytic leukemia with arsenic trioxide", N Engl J Med, vol. 399 No. 19 pp. 1431–1348 (Nov. 5, 1998).
Jing Y et al., "Arsenic trioxide selectively induces acute promyelocytic leukemia cell apoptosis via a hydrogen peroxide–dependent pathway", Blood, vol. 94 No. 6 pp. 2102–2111 (Sep. 15, 1999).
Zhu XH et al., "Apoptosis and growth inhibition in malignant lymphocytes after treatment with arsenic trioxide at clincally achievable concentrations", J Natl Cancer Inst, vol. 91 No. 9 pp. 772–778 (May 5, 1999).
Dai J et al., "Malignant cells can be sensitized to undergo growth inhibition and apoptosis by arsenic trioxide throught modulation of the glutathione redox system", Blood, vol. 93 No. 1 pp. 268–277 (Jan. 1, 1999).
"Arsenic", Mineral Tolerance of Domestic Animals, The National Academy of Sciences–National Research Council, Washington D.C., pp. 40–53 (1980).
Nomoto et al., "Studies on Cardiotonic Agents. I. Synthesis of Some Quinazoline Derrivatives", Chem. Pharm. Bull., vol. 38 No. 6 pp. 1591–1595 (Jun. 1990).
Satoh T, "Reduction of organic compounds with sodium borohydride–transition metal salt systems (1) reduction of organic nitrile, nitro and amide compounds to primary amines", Tetrahedron Letters, vol. 52 pp. 4555–4558 (Nov. 1969).
Andres, R et al., "The Synthesis of Arsonoanilinopyrimidines", J. Am. Chem. Soc., vol. 67 pp. 946–947 (Jan./Jun. 1945).
Uckun FM et al, "Biotherapy of B–cell pecursor leukemia by targeting genistein to CD19–associated tyrosine kinses." Science vol. 267 No. 5199 pp. 886–891 (Feb. 10, 1995).
Waurzyniak B, "In vivo toxicity, pharmacokinetics, and antileukemic activity of TXU (anti–CD7)–pokeweed antiviral protein immunotoxin", Clin Cancer Res, vol. 3 pp. 881–890 (Jun. 1997).
Zhu DM, "Calphostin C triggers calcium–dependent apoptosis in human acute lymphoblastic leukemia cells", Clin Cancer Res, vol. 4 No. 12 pp. 2967–2975 (Dec. 1998).

(List continued on next page.)

Primary Examiner—Deepak R. Rao
(74) Attorney, Agent, or Firm—Merchant & Gould P.C.

(57) ABSTRACT

Novel organic arsenic compounds are described as cytotoxic agents with potent anti-tumor activity against cancer cells and particularly, with regard to human leukemic cells and breast cancer cells.

30 Claims, 16 Drawing Sheets

OTHER PUBLICATIONS

D'Cruz OJ, "Apoptosis–inducing oxovanadium(IV) complexes of 1,10–phenanthroline against human ovarian cancer", *Anti–Cancer Drugs*, vol. 11 No. 10 pp. 849–858 (Nov. 2000).

Gavrieli Y, "Identification of programmed cell death in situ via specific labeling of nuclear DNA fragmentation", *J Cell Biol*, vol. 119 No. 3 pp. 493–501 (Nov. 1992).

Ainley, A. et al., "Trypanocidal activity of some pyrimidylaminophenylarsonic compounds", *Chemical Abstracts*, vol. 53, No. 11, pp. 10243–10245 (Jun. 10, 1959).

Gill, B.S., "Chemotherapeutic Susceptibility of Trypanosoma evansi to some arsenicals and suramin–tryparsamid complex",*Acta Vet.*, vol. 40, No. 2, Abstract only—1 pg. (1971).

Takatsuka, Y. et al., "Various analogs of anthranilic acid and their anti–cancer effects", *Mie Med. J.*, vol. 17, No. 1, Abstract only–1 pg. (1967).

Yuki, H. et al., "Synthesis of Purine and Pyrimidine Derivatives of Arsonic Acid", *Chem. Pharm. Bull.*, vol. 15, No. 7, pp. 1052–1055 (1967).

* cited by examiner

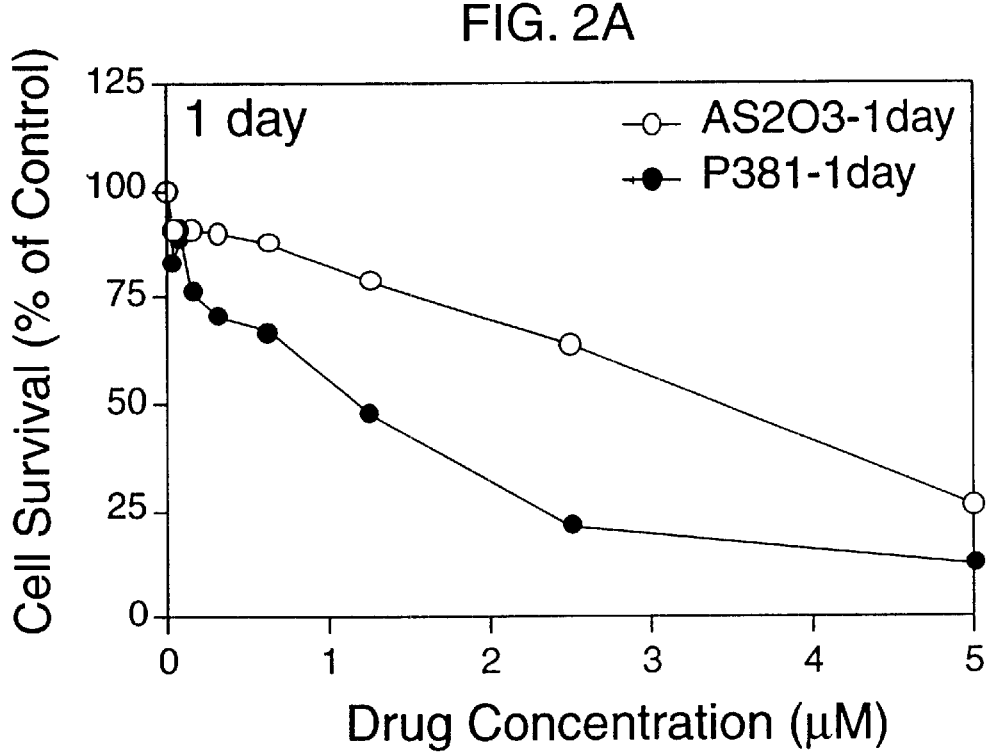

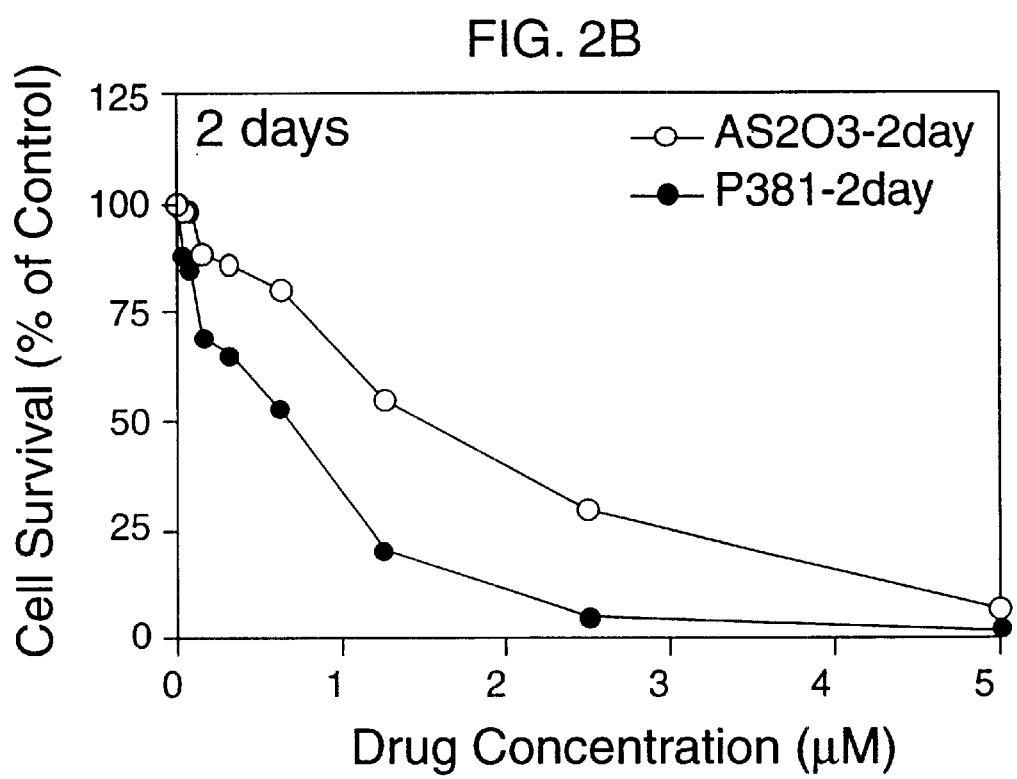

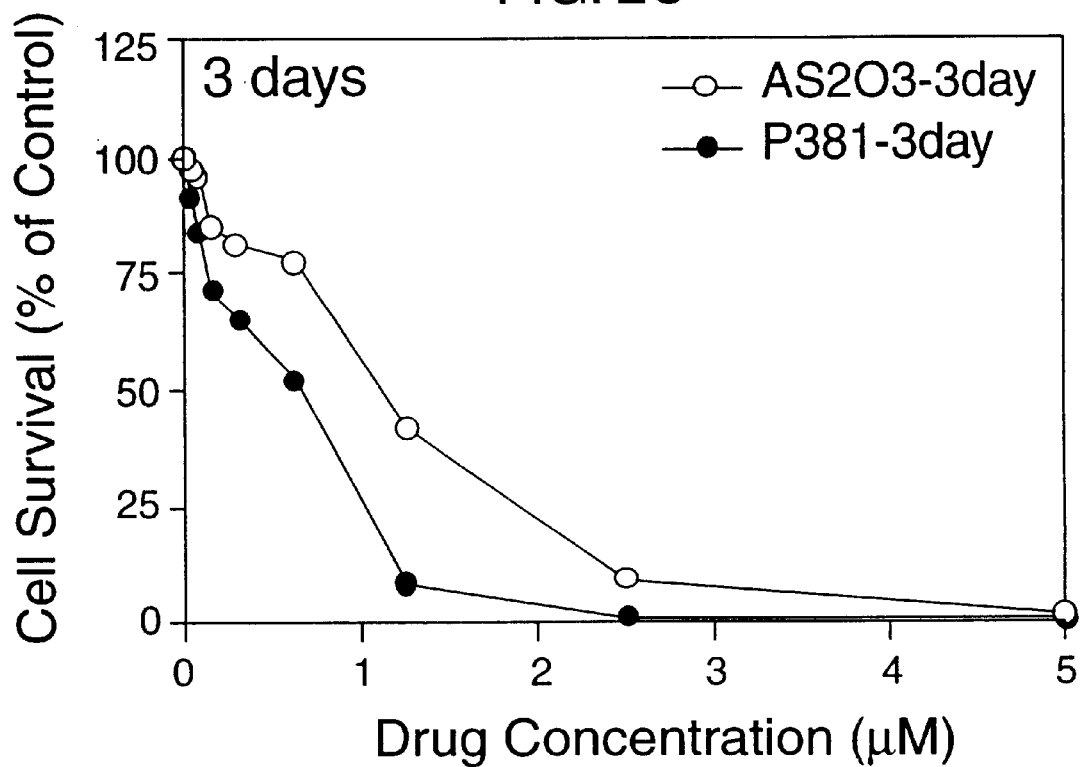

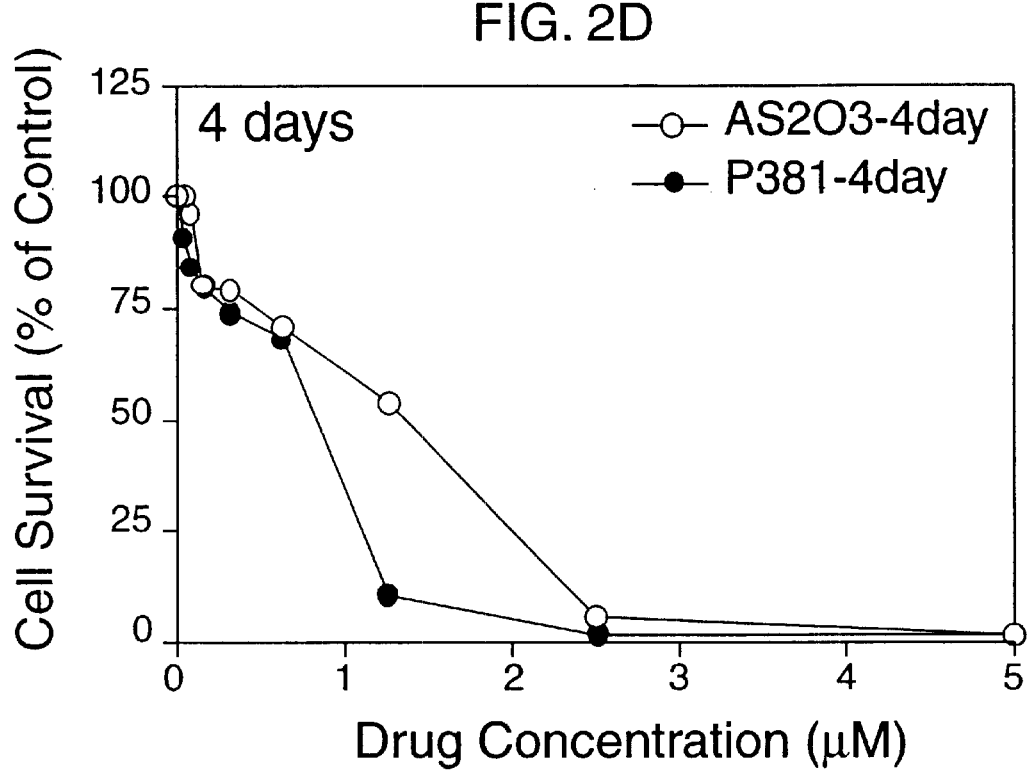

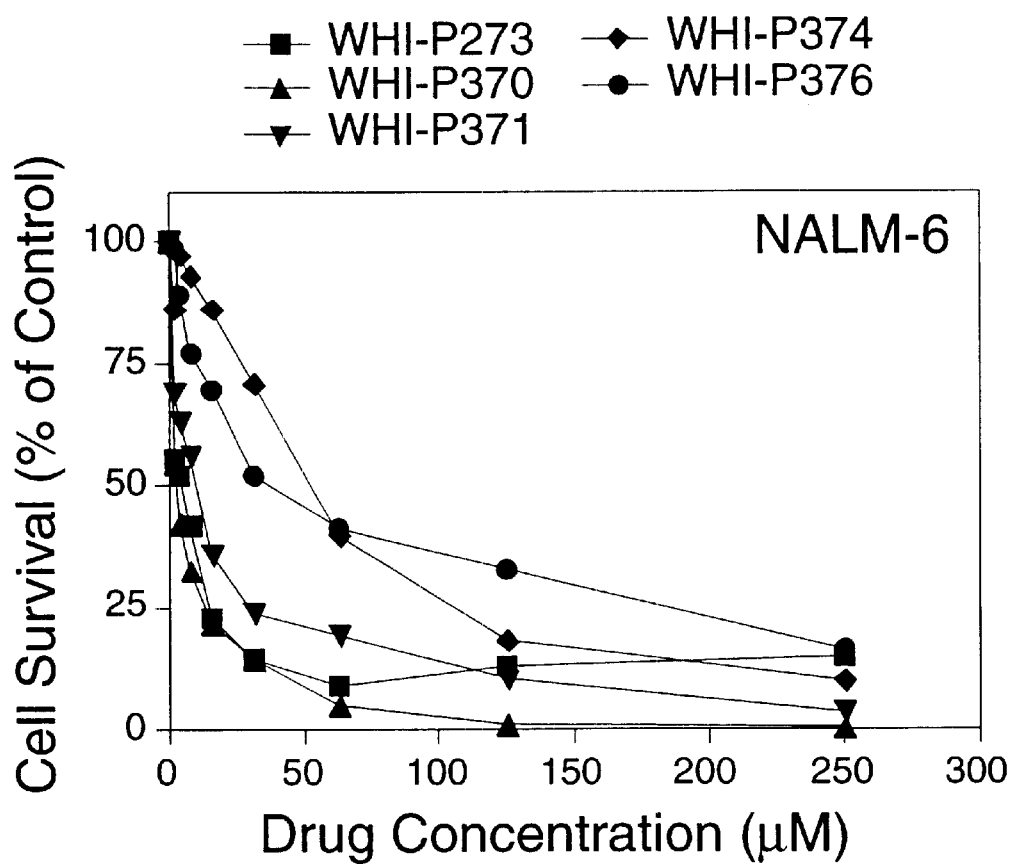

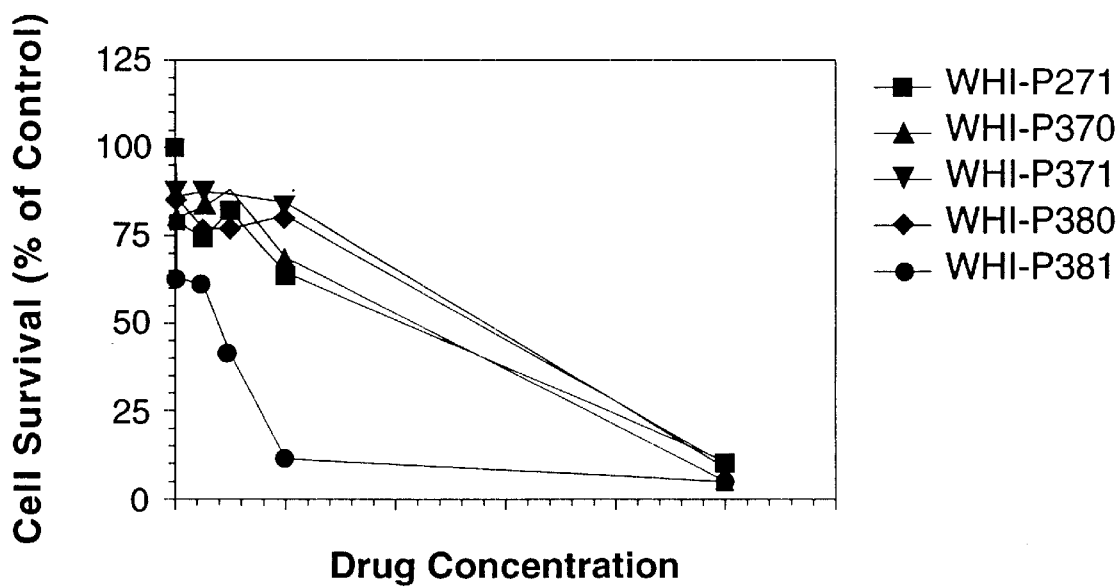

ORGANIC ARSENIC COMPOUNDS

PRIORITY OF INVENTION

This is a continuation of application Ser. No. 09/338,680, filed Jun. 23, 1999 now U.S. Pat. No. 6,191,123, which application claims priority under 35 U.S.C §119(e) from United States Provisional Patent Application No. 60/125,337, filed Mar. 19, 1999.

FIELD OF THE INVENTION

This invention relates to novel organic arsenic compounds for treating tumor cells and which are particularly effective for inducing apoptosis in leukemia and breast tumor cells.

BACKGROUND OF THE INVENTION

Cancer is a major disease that continues as one of the leading causes of death at any age. In the United States alone, it is anticipated that more than a half a million Americans will die of cancer in 1999. Currently, radiotherapy and chemotherapy are two important methods used in the treatment of cancer.

Considerable efforts are underway to develop new chemotherapeutic agents for more potent and specific anti-cancer therapy, presenting effective and efficient cytotoxicity against tumor cells, with minimal interference with normal cell function. Accordingly, there is an urgent need for the development and analysis of novel, effective anti-cancer agents.

SUMMARY OF THE INVENTION

New organic arsenic acid substituted cytotoxic agents with potent anti-tumor activity against cancer cells have been synthesized and examined for their effect on human leukemic cells and breast cancer cells. The compounds were found to exhibit potent cytotoxic activity, particularly against human breast cancer and leukemic cell lines, including primary leukemia cells, at micromolar concentrations.

Accordingly, the present invention includes novel compounds and compositions having potent cytotoxic activity. The present invention also includes methods for treating tumors by administering to a subject an anti-tumor effective amount of a compound of the invention. Compositions of the invention contain an effective or inhibitory amount of a organic arsenic acid substituted compound. The compounds of the invention include those having the following formula:

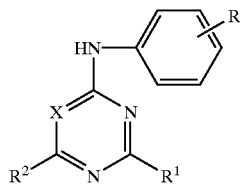

where R is

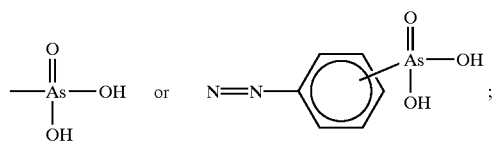

$R^1$ is selected from a group consisting of H, $NR^3R^4$, $SR^3$ and $OR^3$, in which $R^3$ and $R^4$ are each independently hydrogen or a $C_1$–$C_4$ alkyl group. X is N or C. $R^2$ is selected from the group consisting of H, $NR^3R^4$, $SR^3$, $OR^3$, and a group capable of bonding with X, when X is C, to form a fused aromatic or 5- or 6-membered heteroaromatic ring, or a pharmaceutically acceptable salt thereof.

BRIEF DESCRIPTION OF THE DRAWINGS

FIGS. 2A–2D are cell survival graphs demonstrating time and dose-dependent cytotoxic activity of WHI-P381 compared with arsenic trioxide against leukemic NALM-6 cells after 1 (FIG. 2A), 2 (FIG. 1B), 3 (FIG. 1C), and 4 (FIG. 1D) days of treatment.

FIGS. 3A–3F are cell survival graphs demonstrating dose-dependent cytotoxitity of organic arsenic compounds on leukemia ALL (FIGS. 3A–3B), NALM-6 (FIGS. 3C–3D), and MOLT-3 (FIGS. 3E–3D) cells.

FIGS. 4A–4E are cell survival graphs demonstrating the cytotoxic activity of organic arsenic acid substituted compounds against primary leukemic cells. Shown are % survival of cells from five patients (FIGS. 4A–4E) treated with WHI-P273, WHI-P370, WHI-P371, WHI-P380, or WHI-P381.

DETAILED DESCRIPTION OF THE INVENTION

Figure 1A:
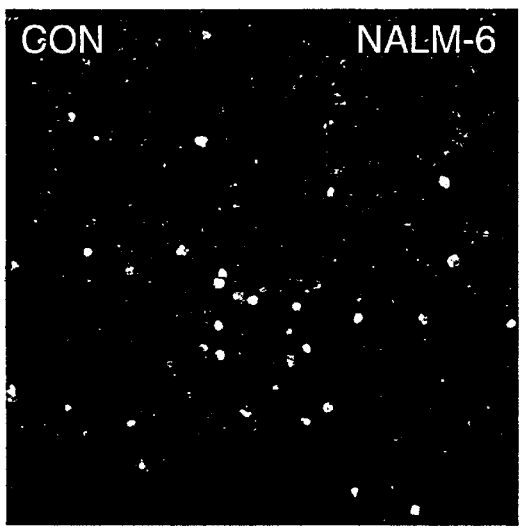
FIGS. 1A–1D are photographs showing cells incubated with 2 µM WHI-P381 for 24 hours, fixed in 2% paraformaldehyde, permeabilized, and visualized for DNA fragmentation (apoptosis assay). Shown are NALM-6 cells untreated (1A) and treated with WHI-P381 (1B); MOLT-3 cells untreated (1C) and treated with WHI-P381 (1D).

The present invention provides novel organic arsenic acid substituted compounds having potent activity as cytotoxic agents. The compounds of the invention are usefull agents in treating tumor cells, for example, against leukemia and breast tumor cells. The organic arsenic acid substituted compounds of the invention are effective in inducing apoptosis in leukemia and breast tumor cells.

Definitions

All scientific and technical terms used in this application have meanings commonly used in the art unless otherwise specified. As used in this application, the following words or phrases have the meanings specified.

As used herein, "alkyl" includes both branched and straight-chain saturated aliphatic hydrocarbon groups having the specified number of carbon atoms. As a preferred embodiment, chains of 1 to 4 carbon atoms are included, for example methyl, ethyl, propyl, isopropyl, butyl, secondary butyl, t-butyl, and the like.

As used herein "halogen" or "halo" substituent includes fluoro, chloro, bromo, and iodo.

As used herein, "fused aromatic ring" includes an unsubstituted or substituted benzene or napthalene ring.

As used herein, "fused heteroaromatic ring" includes a 5- or 6-membered heterocyclic ring having at least one heteroatom selected from nitrogen, oxygen and sulfur.

As used herein, "pharmaceutically acceptable salt thereof" includes an acid addition salt or a base salt.

As used herein, "pharmaceutically acceptable carrier" includes any material which, when combined with a compound of the invention, allows the compound to retain biological activity, such as the ability to induce apoptosis of leukemia or breast tumor cells, and is non-reactive with the subject's immune system. Examples include, but are not limited to, any of the standard pharmaceutical carriers such as a phosphate buffered saline solution, water, emulsions such as oil/water emulsions, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

Compounds of the Invention

The novel organic arsenic acid substituted compounds of the invention have the general structure represented by the following formula I:

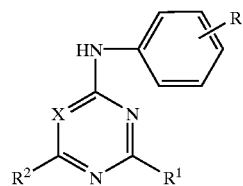

where R is

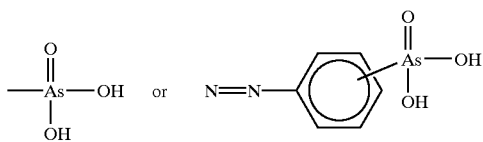

$R^1$ is H, $NR^3R^4$, $SR^3$, $OR^3$, in which $R^3$ and $R^4$ are each independently hydrogen or a $C_1$–$C_4$ alkyl group. Preferably, $R^3$ is hydrogen or methyl, and $R^4$ is hydrogen. X is N or C.

$R^2$ is H, $NR^3R^4$, $SR^3$, $OR^3$, or a group capable of bonding with X, when X is C, to form a fused aromatic or 5- or 6-membered heteroaromatic ring, or a pharmaceutically acceptable salt thereof.

In one embodiment, the fused aromatic ring is preferably a benzene or naphthalene ring, which ring is unsubstituted or substituted by one or more groups selected from halo, hydroxy, mercapto, alkyl of 1–4 carbon atoms, alkoxy of 1–4 carbon atoms, thioalkyl of 1–4 carbon atoms, hydroxyalkyl of 1–4 carbon atoms, $NR^3R^4$, nitro, cyano, $CF_3$, COOH, $SO_3H$, $SO_2NR^3R^4$ in which $R^3$ and $R^4$ are as defined above, and $SO_2F$. More preferably, the fused aromatic ring is a benzene ring unsubstituted or substituted by one or more groups selected from halo, hydroxy, $C_1$–$C_4$ alkoxy or trifluoromethyl. The benzene ring is most preferably 3,4-dimethoxy benzene.

In an alternate embodiment, the fused heteroaromatic ring is preferably a 5- or 6-membered unsaturated heterocyclic ring having at least one heteroatom selected from nitrogen, oxygen and sulfur. More preferably, the fused heteroaromatic ring is a 5-membered ring having at least one nitrogen atom. Most preferably, the 5-membered ring having at least one nitrogen atom, is imidazole.

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as for example silver, zinc, cobalt, and cerium. Examples of suitable amines are N,N'-dibenzylethylenediamine, chloroprocaine, choline, diethanolamine, ethylenediamene, N-methylglucamine, and procaine.

Pharmaceutically acceptable acid addition salts are formed with organic and inorganic acids. Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for the purposes of the invention.

The organic arsenic acid substituted compounds of the present invention can be prepared by the condensation of, for example, quinazoline, pyrimidine, triazine or purine derivatives and a organic arsenic acid derivative as shown in Scheme 1. R, $R^1$ and $R^2$ in Scheme 1 represent the groups previously defined. The reactants, which are either commercially available or prepared by known methods, are heated to reflux in an appropriate solvent for a period of time up to 24 hours. An excess amount of triethylamine is added and the solvent evaporated to afford the crude product which is purified by recrystallization.

Scheme 1

[check formula]

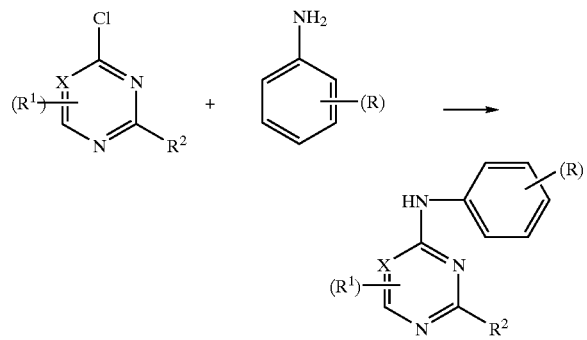

Cytotoxic Compounds

As shown in the examples below, the organic arsenic acid substituted compounds of the invention are effective cytotoxic agents, useful, for example, against tumor cells such as leukemic and breast cancer cells. In the methods of the invention, the cytotoxic effect of these compounds is achieved by contacting the target cell with micromolar amounts of the inhibitory compound.

Particularly useful compounds having potent cytotoxic effects against leukemia cells include:
4-[(6',7'-dimethoxyquinazoline-4')-aminophenylazo]organic arsenic acid (WHI-P273);
2-methylthio-4-[(4'-aminophenylazo)-organic arsenic acid] pyrimidine (WHI-P370);
6-[(4'-aminophenylazo)-organic arsenic acid]-purine (WHI-P371);
2,6-diamino-4[(4'-aminophenylazo)-organic arsenic acid]-1, 3,5-triazine (WHI-P374);
2,6-dimethoxy-4[(4'-aminophenylazo)-organic arsenic acid]-1,3,5-triazine (WHI-P376);

4-(2'-organic arsenic acid)-amino-6,7-dimethoxyquinazoline (WHI-P378);

2-methylthio-4-(4'-organic arsenic acid)-aminopyrimidine (WHI-P380); and 2-methylthio4-(2'-organic arsenic acid)-aminopyrimidine (WHI-P381).

Of these compounds, WHI-P273, WHI-P370, WHI-P371, WHI-P380 and WHI-P381 are particularly potent for inducing apoptosis in leukemia cells. Most useful are WHI-P380 and WHI-P381.

Particularly useful compounds having potent cytotoxic effects against breast cancer cells include WHI-P370, WHI-P374, WHI-P376 and WHI-P381. Of these compounds, WHI-P374, WHI-P376 and WHI-P381 are more particularly potent for inducing apoptosis in breast cancer cells.

WHI-P381 is a particularly useful compound having a potent cytotoxic effect against both leukemia and breast tumor cells.

Tumor Treatment

For purposes of this invention, a method of tumor treatment includes administering to a subject a compound of the invention in order to achieve an inhibition of tumor cell growth, a killing of tumor cells, reduction of tumor size, induction of cellular apoptosis, and/or increased patient survival time.

The cytotoxic compounds of the invention are suitable for use in mammals. As used herein, "mammals" means any class of higher vertebrates that nourish their young with milk secreted by mammary glands, including, for example, humans, rabbits, and monkeys.

Apoptosis

Apoptosis, or programmed cellular death, is an active process requiring new protein synthesis. Typically, the process requires ATP, involves new RNA and protein synthesis, and culminates in the activation of endogenous endonucleases that degrade the DNA of the cell, thereby destroying the genetic template required for cellular homostasis. Apoptosis is observed in controlled deletion of cells during metamorphosis, differentiation, and general cell turnover and appears normally to be regulated by receptor-coupled events. For these reasons, apoptosis has been called "programmed cell death" or "cell suicide." While every cell likely has the genetic program to commit suicide, it is usually suppressed. Under normal circumstances, only those cells no longer required by the organism activate this self-destruction program.

Apoptotic cell death is characterized by plasma membrane blebbing, cell volume loss, nuclear condensation, and endonucleolytic degradation of DNA at nucleosome intervals. Loss of plasma membrane integrity is a relatively late event in apoptosis, unlike the form of cell death termed necrosis, which can be caused by hypoxia and exposure to certain toxins and which is typically characterized early-on by increased membrane permeability and cell rupture.

Administration Methods

The compounds of the present invention can be formulated as pharmaceutical compositions and administered to a mammalian host, including a human patient in a variety of forms adapted to the chosen route of administration. The compounds are preferably administered in combination with a pharmaceutically acceptable carrier, and may be combined with specific delivery agents, including targeting antibodies and/or cytokines.

The compounds can be administered orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes.

More preferably, the compounds of the present invention are administered parenterally, i.e., intravenously or intraperitoneally, by infusion or injection. In one embodiment of the invention, the compounds may be administered directly to a tumor by tumor injection; or by systemic delivery by intravenous injection.

Solutions or suspensions of the compounds can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin.

Sterile injectable solutions are prepared by incorporating the conjugates in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Useful Dose

When used in vivo to kill tumor cells, the administered dose is that effective to have the desired effect, e.g., sufficient to reduce or eliminate tumors. Appropriate amounts can be determined by those skilled in the art, extrapolating using known methods and relationships, from the in vitro data provided in the Examples.

In general, the dose of the novel organic arsenic acid substituted compounds effective to achieve tumor cell apoptosis, reduction in tumors, and increased survival time, is that which administers micromolar amounts of the compound to the cells, preferably 100 micromolar or greater. The required dose is lessened by conjugation of the compound to a targeting moiety, for example, to preferably 100 nanomolar or greater concentrations.

The effective dose to be administered will vary with conditions specific to each patient. In general, factors such as the disease burden, tumor location (exposed or remote), host age, metabolism, sickness, prior exposure to drugs, and the like contribute to the expected effectiveness of a drug. One skilled in the art will use standard procedures and patient analysis to calculate the appropriate dose, extrapolating from the data provided in the Examples.

In general, a dose which delivers about 1–100 mg/kg body weight is expected to be effective, although more or less may be useful.

In addition, the compositions of the invention may be administered in combination with other anti-tumor therapies. In such combination therapy, the administered dose of the organic arsenic acid substituted compounds would be less than for single drug therapy.

Conjugation to a Targeting Moiety

The compound of the invention can be targeted for specific delivery to the cells to be treated by conjugation of the compounds to a targeting moiety. Targeting moiety useful for conjugation to the compounds of the invention include antibodies, cytokines, and receptor ligands expressed on the cells to be treated.

The term "conjugate" means a complex formed with two or more compounds.

The phrase "targeting moiety" means a compound which serves to deliver the compound of the invention to a specific site for the desired activity. Targeting moieties include, for example, molecules which specifically bind molecules present on a cell surface. Such targeting moieties useful in the invention include anti-cell surface antigen antibodies. Cytokines, including interleukins, factors such as epidermal growth factor (EGF), and the like, are also specific targeting moieties known to bind cells expressing high levels of their receptors.

Particularly useful targeting moieties for targeting the compounds of the invention to cells for therapeutic activity include those ligands that bind antigens or receptors present on the tumor cells to be treated. For example, antigens present on B-lineage cancer cells, such as CD19, can be targeted with anti-CD19 antibodies such as B43. Antibody fragments, including single chain fragments, can also be used. IL4 can also be used to target B-cells. Cancer cells expressing EGF or IGF receptors can be targeted with the binding ligand. Other such ligand-receptor binding pairs are known in the scientific literature for specific cancers. Methods for producing conjugates of the compounds of the invention and the targeting moieties are known.

EXAMPLES

The invention may be further clarified by reference to the following Examples, which serve to exemplify some of the embodiments, and not to limit the invention in any way.

Example 1

Synthesis of Substituted Organic Arsenic Compounds

All chemicals were purchased from the Aldrich Chemical Company, Milwaukee, Wis., and were used directly for synthesis. Anhydrous solvents such as acetonitrile, methanol, ethanol, ethyl acetate, tetrahydrofuran, chloroform, and methylene chloride were obtained from Aldrich as sure seal bottles under nitrogen and were transferred to reaction vessels by cannulation. All reactions were carried out under a nitrogen atmosphere.

The organic arsenic acid substituted compounds of the present invention were prepared by the condensation of quinazoline, pyrimidine, triazine or purine and organic arsenic acid according to the procedure shown in Scheme 1.

Scheme 1

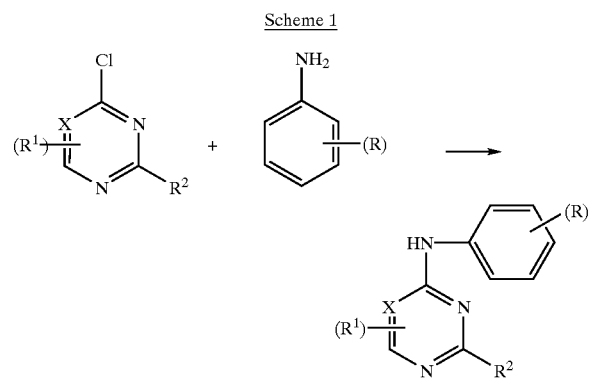

where R is

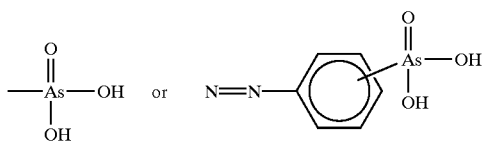

$R^1$ is H, $NR^3R^4$, $SR^3$, $OR^3$, in which $R^3$ and $R^4$ are each independently hydrogen or a $C_1$–$C_4$ alkyl group. Preferably, $R^3$ is hydrogen or methyl, and $R^4$ is hydrogen. X is N or C.

$R^2$ is H, $NR^3R^4$, $SR^3$, $OR^3$, or a group capable of bonding with X, when X is C, to form a fused aromatic or 5- or 6-membered heteroaromatic ring, or a pharmaceutically acceptable salt thereof.

The reactants, which are either commercially available or prepared by known methods, were chosen as appropriate for the synthesis of the compound desired, and heated to reflux in an appropriate solvent for a period of time up to 24 hours. An excess amount of triethylamine was added and the solvent evaporated to afford the crude product which was purified by recrystallization.

Specifically, to prepare WHI-378, a mixture of 4-Cl-quinazoline (2 mmols) and o-Arsanilic acid (3 mmols) in EtOH (20 ml) was heated to reflux. After refluxing for 24 hours, an excess amount of $Et_3N$ was added, and the solvent was concentrated to give the crude product (WHI-378) which was recrystallized from DMF.

Additional compounds, including those shown below in Table 2, were synthesized using this method, and with appropriate reactants.

Example 2

Characterization of Substituted Quinazoline Derivatives

The following organic arsenic acid substituted compounds were synthesized as described above and characterized. Each structure is shown below in Table 1. The identifying analytical test results for each compound are also shown below. Proton and carbon Nuclear Magnetic Resonance ($^1H$ and $^{13}C$ NMR) spectra were recorded on a Mercury 2000 Varian spectrometer operating at 300 MHz and 75 MHz, respectively, using an automatic broad band probe. Unless otherwise noted, all NMR spectra were recorded in $CDCl_3$ at room temperature. $^1H$ chemical shifts are quoted in parts per million (δ in ppm) downfield from tetrarethyl silane (TMS), which was used as an internal standard at 0 ppm and s, d, t, q, m designate singlet, doublet, triplet, quartet and multiplet, respectively. Melting points were determined using a Fisher-Johns melting apparatus and are uncorrected. UV spectra were recorded using a Beckmann Model # DU 7400 UV/V is spectrometer with a cell path length of 1 cm. Methanol was used as the solvent for the UV spectra. Fourier Transform Infrared spectra were recorded using an FT-Nicolet model Protege #460 instrument. The infrared spectra of the liquid samples were run as neat liquids using KBr discs. The KBr pellet method was used for all solid samples. The GC/mass spectrum analysis was conducted using a Hewlett-Packard GC/mass spectrometer model #6890 equipped with a mass ion detector and Chem Station software. The temperature of the oven was steadily increased from 70° C. to 250° C. and the carrier gas was helium.

TABLE 1

Organic Arsenic Acid Substituted Compounds

| No | Ref. | Structure | Formula | MW |
|---|---|---|---|---|
| 1 | P-273 | 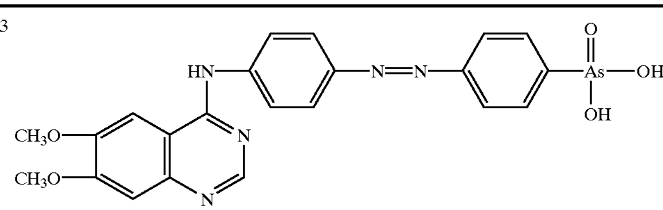 | $C_{22}H_{19}AsN_5O_5$ | 508 |
| 2 | P-370 | 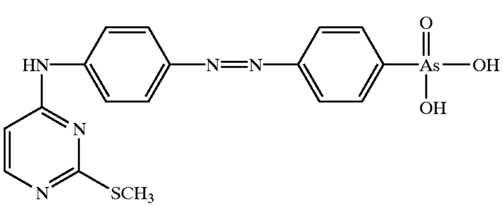 | $C_{17}H_{16}AsN_5O_3S$ | 445 |
| 3 | P-371 | 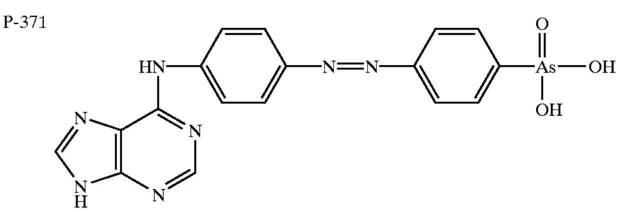 | $C_{17}H_{14}AsN_7O_3$ | 439 |
| 4 | P-374 | 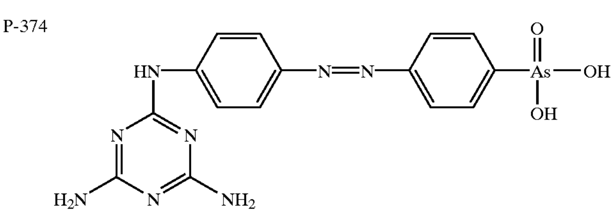 | $C_{15}H_{15}AsN_8O_3$ | 430 |

TABLE 1-continued

Organic Arsenic Acid Substituted Compounds

| No | Ref. | Structure | Formula | MW |
|----|------|-----------|---------|-----|
| 5 | P-378 | 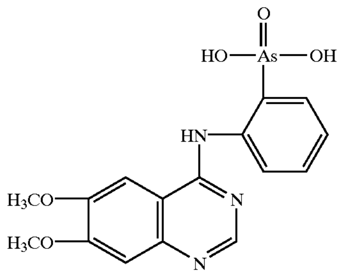 | $C_{16}H_{16}AsN_3O_5$ | 405 |
| 6 | P-379 | 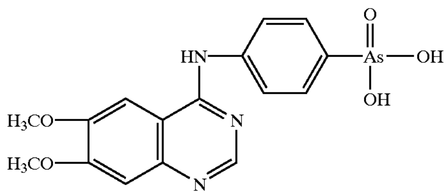 | $C_{16}H_{16}AsN_3O_5$ | 405 |
| 7 | P-380 | 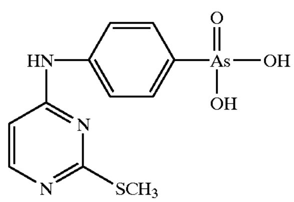 | $C_{11}H_{12}AsN_3O_3S$ | 341 |
| 8 | P-381 | 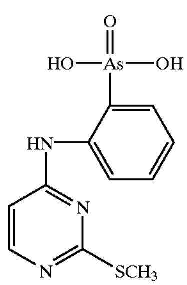 | $C_{11}H_{12}AsN_3O_3S$ | 341 |
| 9 | P-385 | 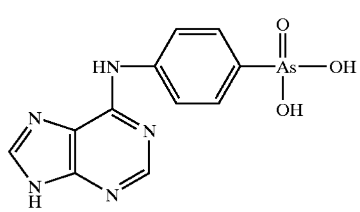 | $C_{11}H_{10}AsN_5O_3$ | 335 |
| 10 | P-386 | 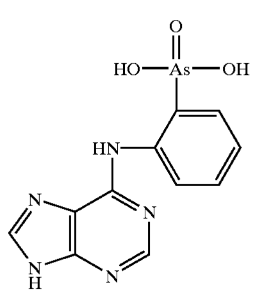 | $C_{11}H_{10}AsN_5O_3$ | 335 |

4-[(6',7'-Dimethoxyquinazoline-4')-aminophenylazo]phenyl arsenic acid (WHI-P273)

The yield 71.20%; m.p.>300.0° C. $^1$H NMR(DMSO-d$_6$). δ8.83(s, 1H, 2-H) 8,35(s, 1H, 5-H), 8.18–7.97 (m, 8H, Ph—H), 7.37(s, 1H, 8-H), 4.05(s, 3H, —OCH$_3$), 3.99(s, 3H, —OCH$_3$). UV(MeOH): 204.0, 215.0, 250.0, 330.0 nm IR(KBr)υ$_{max}$: 3431, 2629, 1675, 1580 cm$^{-1}$. Found: C,40.91; H,3.35; N, 10.56 C$_{23}$H$_{22}$AsN$_5$O$_5$.4HCl requires: C, 41.37; H, 3.90; N, 10.47%.

2-Methylthio-4-[(4'-aminophenylazo)-phenyl arsenic acid] pyrimidine(WHI-P370)

The yield 86.50%;. m.p. 240.0–242.0° C. $^1$H NMR (DMSO-d$_6$): δ11.57(s, 1H, —NH), 8.23 (d, 1H, J=6.3 Hz, 5-H), 8.07–7.92 (m, 8H, Ph—H), 6.94(d, 1H, J=6.3 Hz, 6-H), 2.61(s, 3H, —SCH$_3$). UV(MeOH): 205.0, 215.0, 250.0, 330.0 nm. IR(KBr)υ$_{max}$: 3531, 2638, 1685, 1574 cm$^{-1}$.

6-[(4'-Aminophenylazo)-phenyl arsenic acid]-purine (WHI-P371)

The yield 81.30%; m.p.>300.0° C. $^1$H NMR(DMSO-$_6$): δ11.61(s, 1H, —NH), 9.56(s, broad, 3H, -9-NH, —As(OH)$_2$), 8.23 (d, 1H, J=6.3 Hz, 5-H), 8.83(s, 1H, -2H), 8.77(s, 1H, -8H), 8.32–7.91 (m, 8H, Ph—H) 6.94(d, 1H, J=6.3 Hz, 6-H), 2.61(s, 3H, —SCH$_3$). UV(MeOH): 200.0, 213.0, 247.0, 328.0 nm. IR(KBr)υ$_{max}$: 3549, 2638, 1674, 1574 cm$^{-1}$.

2,6-Diamino-4[(4'-aminophenylazo)-phenyl arsenic acid]-1,3,5-triazine (WHI-P374)

The yield 79.50%; m.p.>300.0° C. $^1$H NMR(DMSO-d$_6$): δ12.04(s, 1H, —NH), 8.01–7.70(m, 8H, Ph—H), 5.81(s, broad, 6H, —NH$_2$, —As(OH)$_2$). UV(MeOH): 200.0, 213.0, 247.0, 328.0 nm. IR(KBr)υ$_{max}$: 3400–3500, 2638, 1674, 1574 cm$^{-1}$.

2,6-Dimethoxyl-4[(4'-aminophenylazo)-phenyl arsenic acid]-1,3,5-triazine (WHI-P376)

Yield 82.43%; m.p.>300.0° C. $^1$H NMR(DMSO-d$_6$): δ11.17(s, 1H, —NH), 7.99–6.71(m, 8H, Ph—H), 3.86(s, 6H, —OCH$_3$). UV(MeOH): 203.0, 214.0, nm. IR(KBr)υ$_{max}$: 3350–3550, 2640, 1633, cm$^{-1}$.

4-(2'-phenyl arsenic acid)-amino-6,7-dimethoxyquinazoline (WHI-P378)

The yield 83.20%; m.p.>300.0° C. $^1$H NMR(DMSO-d$_6$): δ8.89(s, 1H, 2-H), 8,21(s, 1H, 5-H), 8.46–7.51 (m, 4H, Ph—H), 7.40(s, 1H, 8-H), 3.99(s, 6H, —OCH$_3$). UV(MeOH): 208.0, 225.0, 253.0, 328.0 nm. IR(KBr)υ$_{max}$: 3431, 2629, 1685, 1580 cm$^{-1}$.

4-(4'-phenyl arsenic acid)-amino-6,7-dimethoxyquinazoline (WHI-P379)

The yield 85.40%; m.p.>300.0° C. $^1$H NMR(DMSO-d$_6$): δ11.33(s, 1H, —NH), 8.23 (d, 1H, J=6.3 Hz, 5-H), 8.89(s, 1H, -2H), 8.26 (s, 1H, -8H), 8.32–7.91 (m, 8H, Ph—H) 6.94(d, 1H, J=6.3 Hz, 6-H), 2.61(s, 3H, —SCH$_3$). UV(MeOH): 200.0, 213.0, 247.0, 328.0 nm. IR(KBr)υ$_{max}$: 3549, 2638, 1674, 1574 cm$^{-1}$.

2-Methylthio-4-(4'-phenyl arsenic acid)-aminopyrimidine (WHI-P380)

The yield 82.50%; m.p.>300.0° C. $^1$H NMR(DMSO-d$_6$): δ11.19(s, 1H, —NH), 9.82(s, broad, 2H, —As(OH)$_2$), 8.22 (d, 1H, J=6.3 Hz, 5-H), 7.98 (d, 2H, J=8.4 Hz, 2',6'-H),), 7.89 (d, 2H, J=8.4 Hz, 3',5'-H), 6.82 (d, 1H, J=6.3 Hz, 6-H), 2.58(s, 3H, —SCH$_3$). UV(MeOH): 205.0, 213.0, 247.0, 328.0 nm. IR(KBr)υ$_{max}$: 3400–3550, 2638, 1654, 1580 cm$^{-1}$.

2-Methylthio-4-(2'-phenyl arsenic acid)-aminopyrimidine (WHI-P381)

The yield 86.40%; m.p. 225.0–228.0° C. $^1$H NMR (DMSO-d$_6$): δ10.94(s, 1H, —NH), 8.46 (d, 1H, J=8.1 Hz, 5-H), 8.21–7.23(m, 4H, 3', 4', 5', 6'-H), 6.47(d, 1H, J=8.1 Hz, 6-H), 2.49(s, 3H, —SCH$_3$). $^{13}$C NMR(DMSO-d$_6$): δ170.7 (2-C), 159.0(4-C), 156.1(6-C), 141.7(5-C), 133.9(1'-C), 131.5(6'-C), 123.3, 121.9, 121.0(3', 4', 5'-C), 103.6(2'-C), 13.8(SCH$_3$—C). UV(MeOH): 201.0, 213.0, 247.0, 328.0 nm. IR(KBr)υ$_{max}$: 3420–3550, 2638, 1664, 1583 cm$^{-1}$.

6-(4'-phenyl arsenic acid)-aminopurine (WHI-P385)

The yield 71.30%; m.p.>300.0° C. $^1$H NMR(DMSO-d$_6$): δ11.17(s, 1H, 6-NH), 10.11(s, broad, 3H, 9-NH, As(OH)$_2$), 8.71 (s, 1H, 2-H), 8.67(s, 1H, 8-H), 8.24 (d, 2H, J=8.7 Hz, 2', 6'-H), 7.79(d, 2H, J=8.7 Hz, 3', 5'-H). UV(MeOH): 205.0, 213.0, 247.0, 328.0 nm. IR(KBr)υ$_{max}$: 3350–3560, 2638, 1678, 1582 cm$^{-1}$.

6-(2'-phenyl arsenic acid)-aminopurine (WHI-P386)

The yield 73.40%; m.p. 288.0–290.0° C. $^1$H NMR (DMSO-d$_6$): δ11.34(s, 1H, 6-NH), 8.75 (3, 1H, 9-NH), 8.47(s,1H,2-H), 8.34(s, 1H, 8-H), 8.04–7.27(m, 4H, 3', 4', 5', 6'-H). UV(MeOH): 201.0, 213.0, 247.0, 328.0 nm. IR(KBr) υ$_{max}$: 3430–3560, 2638, 1664, 1583 cm$^{-1}$.

Example 3

Cytotoxicity of Organic Arsenic Acid Substituted Compounds

The cytotoxicity of the organic arsenic acid substituted compounds against specific tumor cells was evaluated using the MTT assay described below.

Cytotoxicity Assay

The cytotoxicity assay of various compounds against tumor cells was performed using the MTT (3-[4,5-dimethylthiazol-2-yl]-2,5-diphenyl tetrazolium bromide) assay (Boehringer Mannheim Corp., Indianapolis, Id.). Unless otherwise specified, all cell lines were obtained from the American Type Culture Collection (ATCC). Briefly, exponentially growing cells were seeded into a 96-well plate at a density of 2.5×10$^4$ cells/well and incubated for 36 hours at 37° C. prior to drug exposure. On the day of treatment, culture medium was carefully aspirated from the wells and replaced with fresh medium containing the organic arsenic acid substituted compounds WHI-P273, WHI-P370, WHI-P371, WHI-P374, WHI-P376, WHI-P378, WHI-P379, WHI380, WMI381, WHI-P385, or WHI-P386 at concentrations ranging from 0.1 to 250 μM. Triplicate wells were used for each treatment.

Human leukemic cell lines (NALM-6, MOLT-3, ALL1, and RS4;11) and human breast tumor cell line (BT20) were obtained from the American Type Culture Collection and maintained as a continuous cell line in Dulbecco's modified Eagles's medium supplemented with 10% fetal bovine serum and antibiotics.

The cells were incubated with the various compounds for 24–36 hours at 37° C. in a humidified 5% CO$_2$ atmosphere. To each well, 10 μl of MTT (0.5 mg/ml final concentration) was added and the plates were incubated at 37° C. for 4 hours to allow MTT to form formazan crystals by reacting with metabolically active cells. The formazan crystals were solubilized overnight at 37° C. in a solution containing 10% SDS in 0.01 M HCl. The absorbence of each well was measured in a microplate reader (Labsystems) at 540 nm and a reference wavelength of 690 nm. To translate the OD$_{540}$ values into the number of live cells in each well, the OD$_{540}$ values were compared to those on standard OD$_{540}$—versus—cell number curves generated for each cell line. The percent survival was calculated using the formula:

$$\% \text{ Survival} = \frac{\text{live cell number [test]}}{\text{live cell number [control]}} \times 100$$

The $IC_{50}$ values for cytotoxic activity were calculated by non-linear regression analysis, and are shown below in Table 2.

TABLE 2

Cytotolic Activity of Organic arsenic Acid Substituted Compounds against leukemkic (NALM-6, MOLT-3, ALL1, RS4;11) and breast cancer (BT20) cells.

| Drug | NALM-6 $IC_{50}$ ($\mu M$) | MOLT-3 $IC_{50}$ ($\mu M$) | ALL1 $IC_{50}$ ($\mu M$) | RS4;1 1 $IC_{50}$ ($\mu M$) | BT20 $IC_{50}$ ($\mu M$) |
|---|---|---|---|---|---|
| WHI-P273 | 7.3 | 12.1 | 8.2 | 7.7 | >250 |
| WHI-P370 | 5.98 | 2.9 | 1.9 | 4.8 | 67.8 |
| WHI-P371 | 15.2 | 21.6 | 24.5 | 16.2 | >250 |
| WHI-P374 | 50.1 | 103.6 | 55.8 | 53.6 | 13.9 |
| WHI-P376 | 64.8 | 50.4 | 29.1 | 23.3 | 21.5 |
| WHI-P378 | 46.6 | 67.3 | 128.3 | 114.7 | >250 |
| WHI-P380 | 1.7 | 14.2 | 6.2 | 10.2 | 238.6 |
| WHI-P381 | <1.9 | <1.9 | <1.9 | <1.9 | 17.3 |
| WHI-P386 | 30.8 | >250 | >250 | >250 | >250 |

Each of the organic arsenic substituted compounds used in this study exhibited a potent cytotoxic effect against at least one of the tumor cells used. Compounds, WHI-P370, WHI-P374, WHI-P376 and WHI-P381 were cytotoxic against the breast cancer cell line, BT20, while compounds WHI-P273, WHI-P370, WHI-P371, WHI-P376, WHI-P380 and WHI-P381 were cytotoxic for all of the leukemic cell lines used. As shown in Table 2, WHI-P380 and WHI-P381 exhibited highest cytotoxic activity, causing cell death in leukemic cell lines at micromolar concentrations with $IC_{50}$ values of 1.7 to 14.2 $\mu M$ (WHI-P380) and 1.9 $\mu M$ (WHI-P381).

Figure 3A:
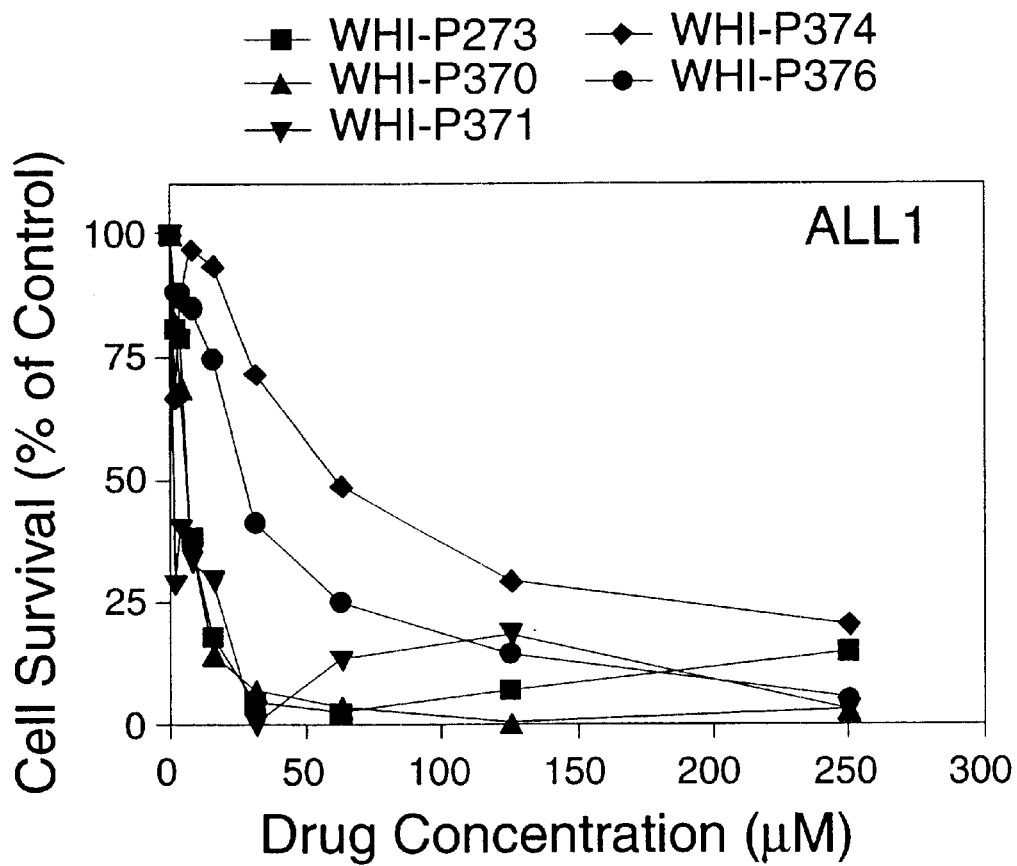
Figure 3B:
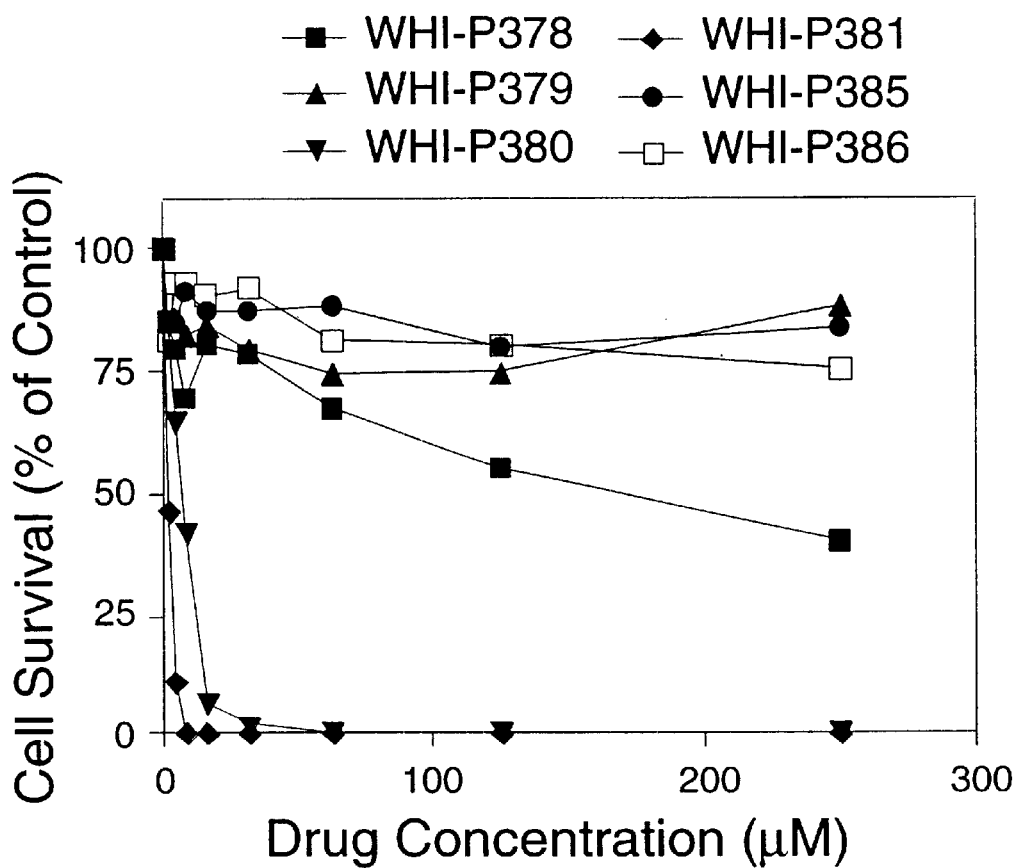
Figure 3D:
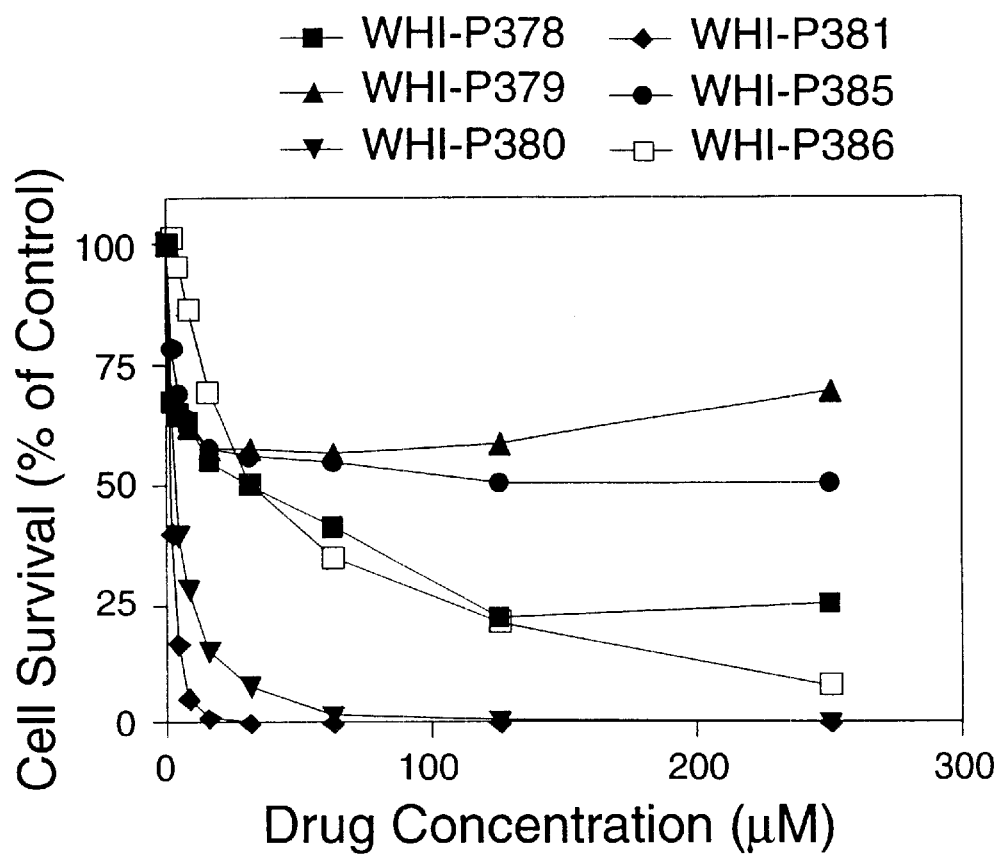
Figure 3E:
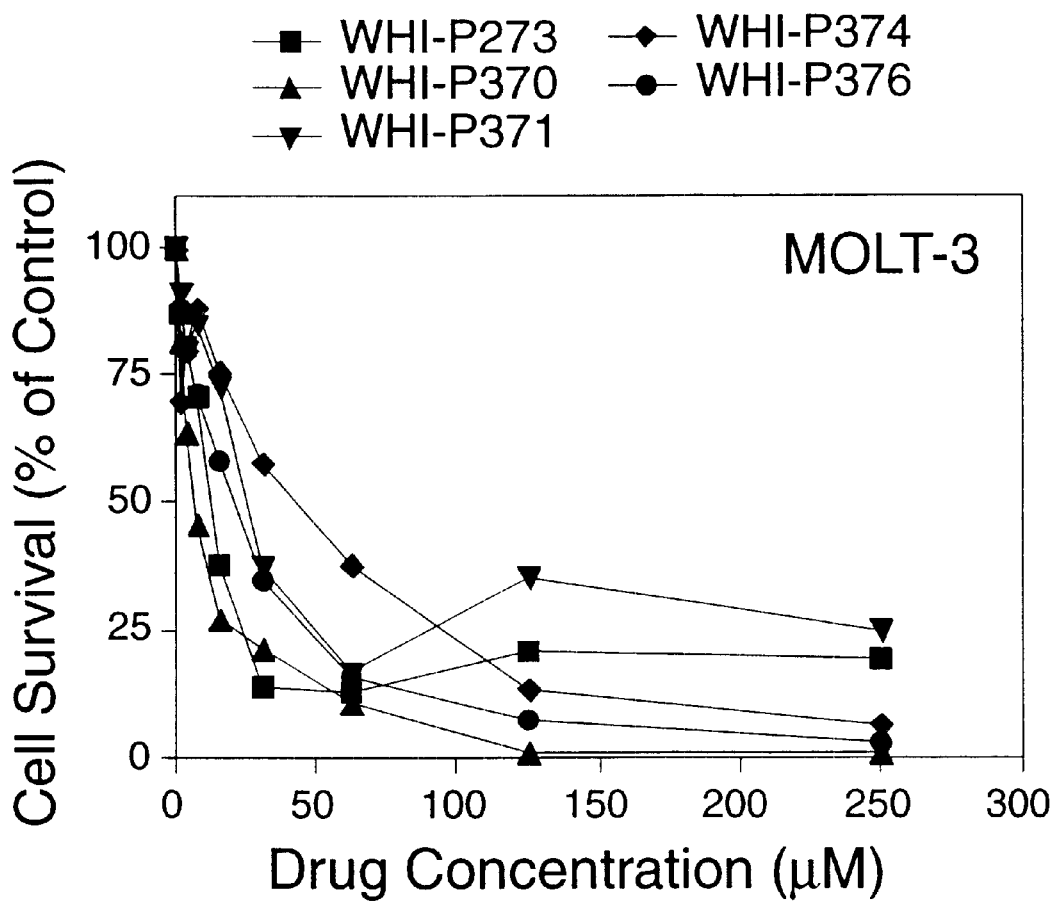
Figure 3F:
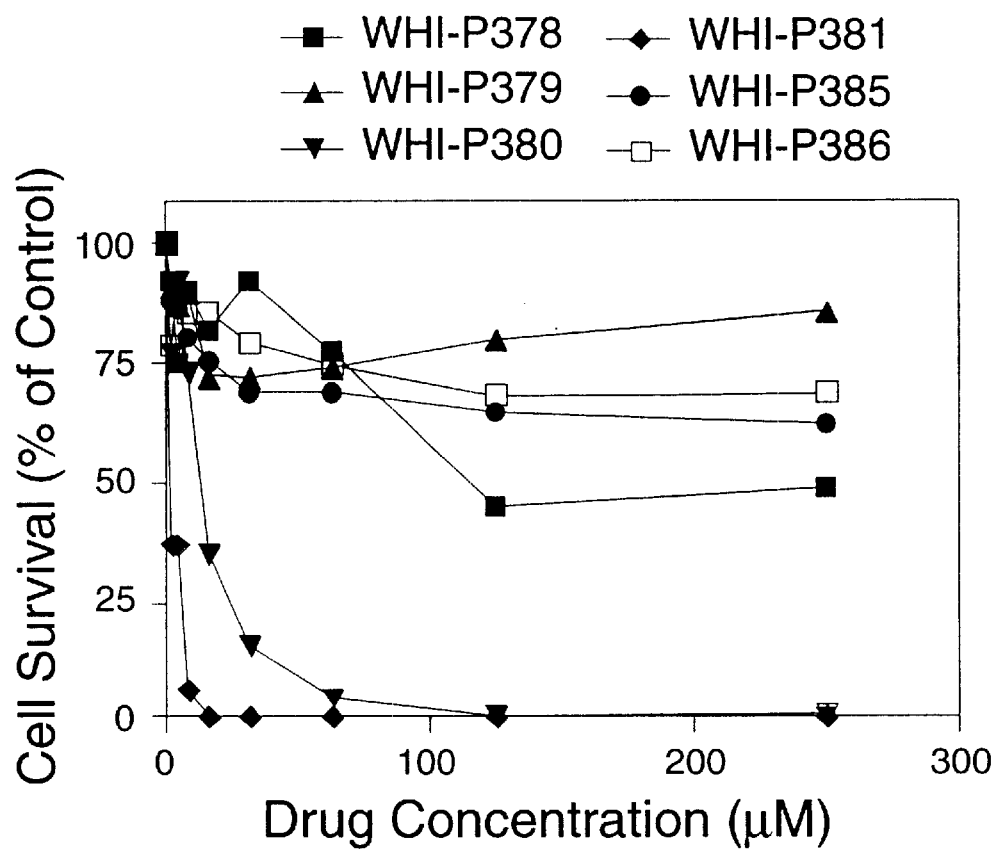

The dose-responsive ant-proliferative activity of various organic arsenic acid substituted compounds against leukemic cell lines (NALM-6 and MOLT-3) is shown below in Table 3. FIGS. 3A–3F show dose response curves in ALL1, NALM-6, and MOLT-3 cells.

TABLE 3

Anti-proliferative Activity of Organic Arsenic Substituted Compounds Against Leukemic Cell Lines.

| Drug | Cell Line | Concentration (mM) | Mean No. of Colonies/$10^6$ Cells | % Inhibition |
|---|---|---|---|---|
| WHI-P273 | NALM-6 | 0 | 4123 (4068, 4364) | — |
| | | 0.1 | 3638 (3260, 4016) | 13.7 |
| | | 1 | 61 (24,96) | 98.5 |
| | | 10 | 0 | 100 |
| | | 100 | 0 | 100 |
| | MOLT-3 | 0 | 1056 (1000, 1112) | — |
| | | 0.1 | 1230 (968, 1492) | — |
| | | 1 | 264 (216,312) | 75 |
| | | 10 | 0 | 100 |
| | | 100 | 0 | 100 |
| WHI-P370 | NALM-6 | 0 | 4216 (4068, 4364) | — |
| | | 0.1 | 2194 (2860, 2968) | 30.9 |
| | | 1 | 0 | 100 |
| | | 10 | 0 | 100 |
| | | 100 | 0 | 100 |
| | MOLT-3 | 0 | 1056 (1000, 1112) | — |
| | | 0.1 | 992 (896, 1088) | 6.1 |
| | | 1 | 0 | 100 |
| | | 10 | 0 | 100 |
| | | 100 | 0 | 100 |
| WHI-P371 | NALM-6 | 0 | 4216 (4068, 4364) | — |
| | | 0.1 | 3846 (3696,3996) | 8.8 |
| | | 1 | 994 (616, 1372) | 76.4 |
| | | 10 | 0 | 100 |
| | | 100 | 0 | 100 |
| | MOLT-3 | 0 | 1056 (1000, 1112) | — |
| | | 0.1 | 1098 (1004, 1192) | — |
| | | 1 | 761 (678, 844) | 27.9 |
| | | 10 | 0 | 100 |
| | | 100 | 0 | 100 |
| WHI-P380 | NALM-6 | 0 | 1208 (864, 1552) | — |
| | | 0.1 | 400 (116, 684) | 66.9 |
| | | 1 | 2 (3, 1) | 99.8 |
| | | 10 | 0 | 100 |
| | | 100 | 0 | 100 |
| | MOLT-3 | 0 | 1438 (1424, 1452) | — |
| | | 0.1 | 678 (624, 732) | 52.8 |
| | | 1 | 436 (272, 600) | 69.7 |
| | | 10 | 0 | 100 |
| | | 100 | 0 | 100 |
| WHI-P381 | NALM-6 | 0 | 1208 (864, 1152) | — |
| | | 0.1 | 0 | 100 |
| | | 1 | 0 | 100 |
| | | 10 | 0 | 100 |
| | | 100 | 0 | 100 |
| | MOLT-3 | 0 | 1438 (1424, 1452) | — |
| | | 0.1 | 429 (202, 656) | 70.2 |
| | | 1 | 0 | 100 |
| | | 10 | 0 | 100 |
| | | 100 | 0 | 100 |

Example 4

Organic Arsenic Acid Substituted Compounds Induce Apoptosis in Cancer Cells

In situ Detection of Apoptosis

Assay for apoptosis was performed by the in situ nick-end-labeling method using an ApopTag in situ detection kit (Oncor, Gaithersburg, Md.) according to the manufacturer's recommendations. Exponentially growing cells (NALM-6 and MOLT-3) were seeded in 6-well tissue culture plates at a density of $50 \times 10^4$ cells/well and cultured for 36 hours at 37° C. in a humidified 5% $CO_2$ atmosphere. The supernatant culture medium was carefully aspirated and replaced with fresh medium alone or fresh medium containing WHI-P381 at a concentration of 2 $\mu$g/ml.

After a 36 hour incubation at 37° C. in a humidified 5% $CO_2$ incubator, the supernatants were carefully aspirated and the cells were treated for 1–2 minutes with 0.1% trypsin. The detached cells were collected into a 15 ml centrifuge tube, washed with medium and pelleted by centrifugation at 1000 rpm for 5 minutes. Cells were resuspended in 50 $\mu$l of PBS, transferred to poly-L-lysine coated coverslips and allowed to attach for 15 minutes. The cells were washed once with PBS and incubated with equilibration buffer for 10 minutes at room temperature.

After removal of the equilibration buffer, cells were incubated for 1 hour at 37° C. with the reaction mixture containing terminal deoxynucleotidyl transferase (TdT) and digoxigenin-11-UTP for labeling of exposed 3'-hydroxyl ends of fragmented nuclear DNA. The cells were washed with PBS and incubated with anti-digoxigenin antibody conjugated to FITC for 1 hour at room temperature to detect the incorporated dUTP. After washing the cells with PBS, the coverslips were mounted onto slides with Vectashield containing propidium iodide (Vector Labs, Burlingame, Calif.) and viewed with a confocal laser scanning microscope. Non-apoptotic cells do not incorporate significant amounts of dUTP due to lack of exposed 3-hydroxyl ends, and consequently have much less fluorescence than apoptotic cells, which have an abundance of exposed 3'-hydroxyl ends. In control reactions, the TdT enzyme was omitted from the reaction mixture.

Results

Figure 1B:
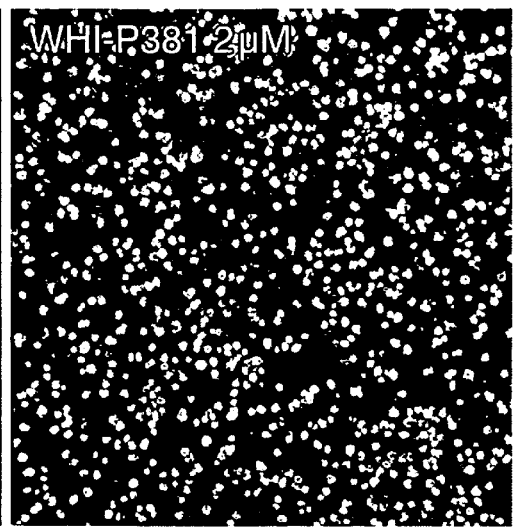
Figure 1C:
Figure 1D:
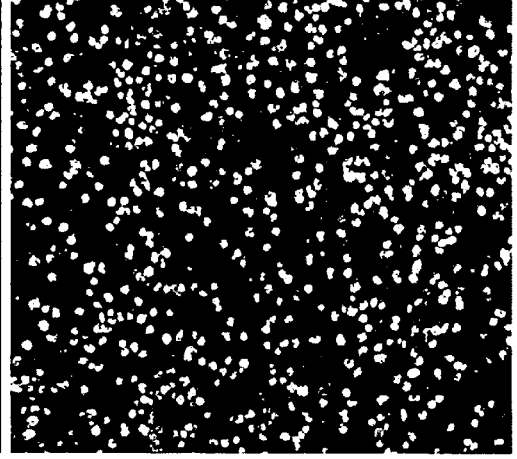

The ability of the organic arsenic substituted compound, WHI-P381, to induce apoptotic cell death in leukemic cell lines, NALM-6 and MOLT-3, is shown in FIG. 1. Treated cells, NALM-6 (FIG. 1B) and MOLT-3 (FIG. 1D) showed a much greater Fluorescence, percentage of apoptosis, than untreated cells, NALM-6 (FIG 1A) and MOLT-3 (FIG. 1C). These results demonstrate the apoptosis-inducing activity of the compounds of the invention.

Example 5

Organic Arsenic Compounds are more Potent than Arsenic Trioxide

Leukemic NALM-6 cells were treated with WHI-P381 or arsenic trioxide at doses from 0.07 µM to 5 µM for 1, 2, 3 or 4 days. Cell survival was assessed by the MTT assay and $IC_{50}$ calculated as described above. Surprisingly, as shown in FIGS. 2A–2D, the organic arsenic acid substituted compound, WHI-P381 was more cytotoxic than arsenic trioxide, which has been shown to induce apoptosis in refractory acute promyelic leukemia cells, B-cell leukemic cells and megakaryocytotic leukemia cell line. The time and dose-dependent activity of WHI-P381 in comparison with arsenic trioxide is shown in FIGS. 2A–2D. The $IC_{50}$ values for WHI-P381 are shown in Table 4 below, and demonstrate the more potent activity of the organic arsenic compound of the invention over arsenic trioxide.

TABLE 4

Cytotoxicity against NALM-6 cells.

| | $IC_{50}$ (µM) | | | |
|---|---|---|---|---|
| | Day 1 | Day 2 | Day 3 | Day 4 |
| WHI-P381 | 2.03 | 0.85 | 0.7 | 0.68 |
| Arsenic trioxide | 3.8 | 3.2 | 2.0 | 1.2 |

Example 6

Figure 4A:
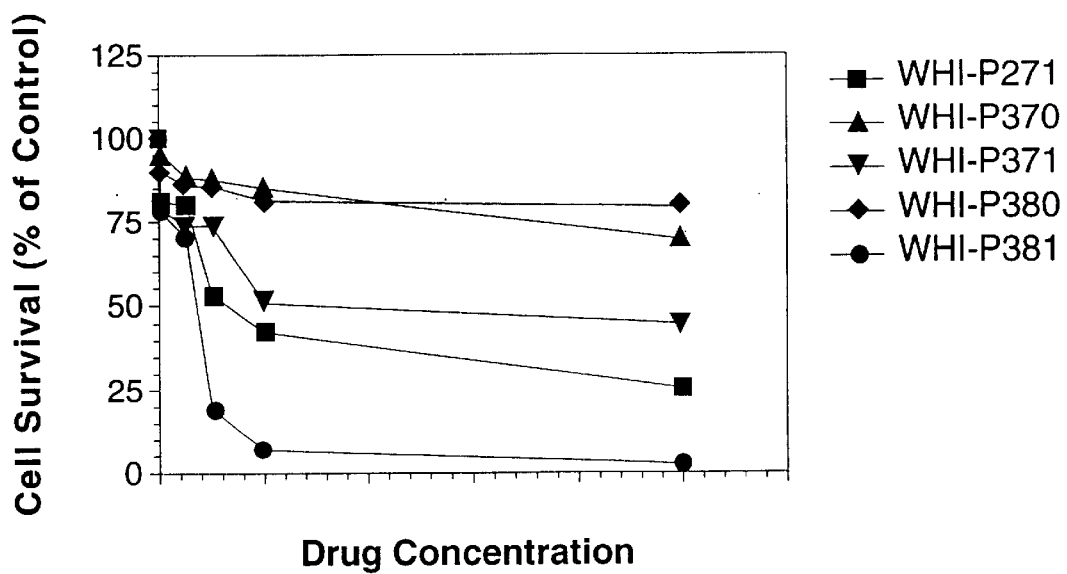
Figure 4B:
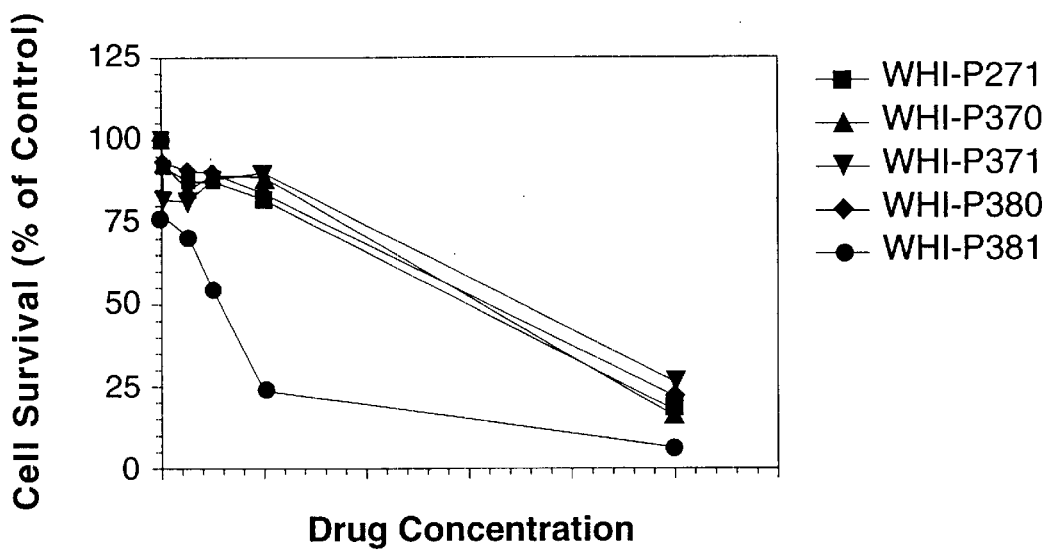
Figure 4D:
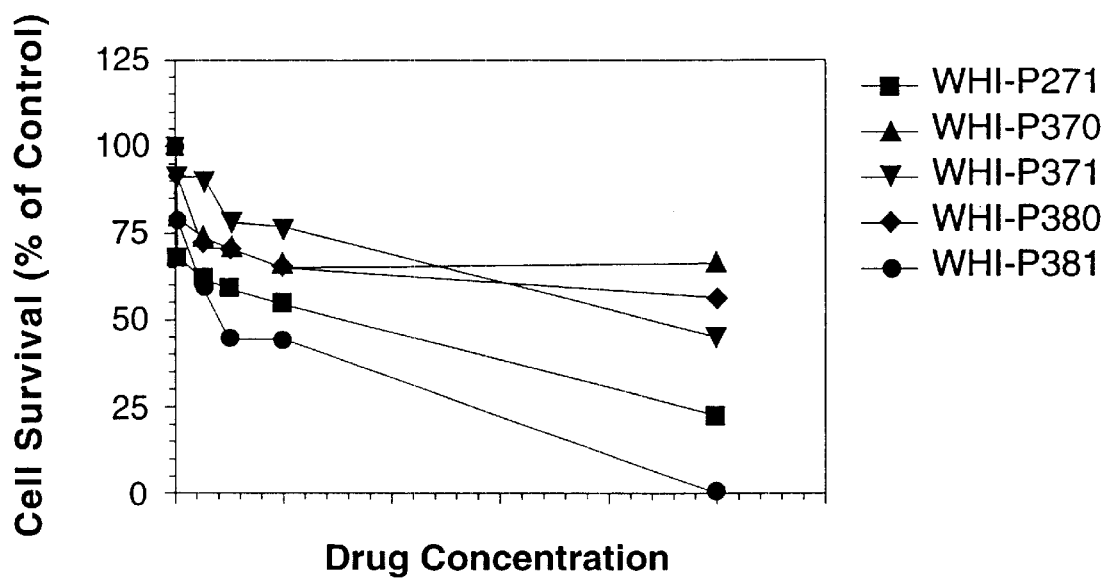
Figure 4E:
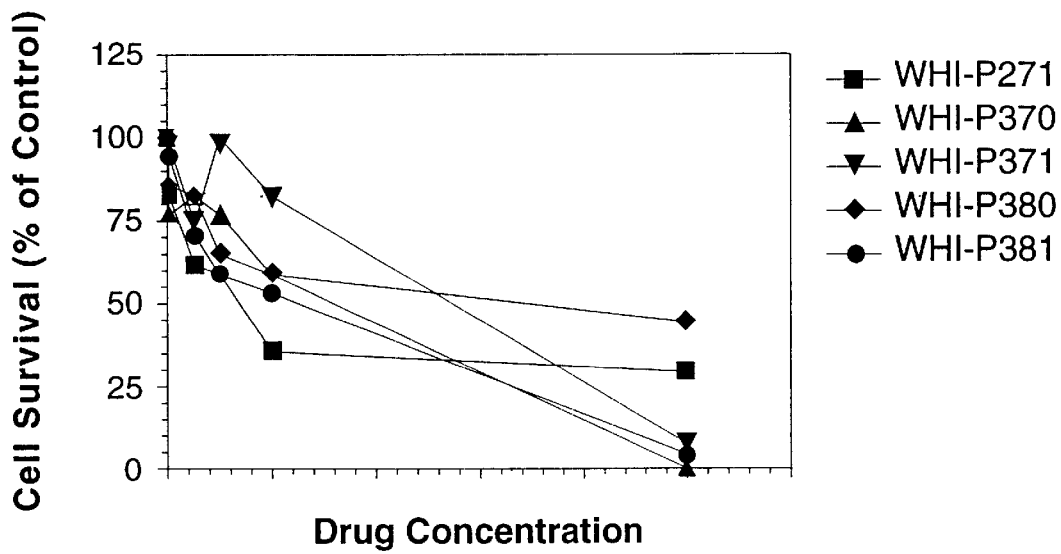

Organic Arsenic Acid Substituted Compounds are Cytotoxic to Primary Leukemic Cells The cytotoxic activity of a variety of organic arsenic acid substituted compounds against primary leukemic cells was determined using MTT assays as described above. Cells obtained from 5 leukemia patients were treated with WHI-P273, WHI-P370, WHI-P371, WHI-P380 and WHI-P381 according to the methods described above for cell lines. Cytotoxicity was assessed by the methods described above. The data are presented in FIGS. 4A–4E, and demonstrate that primary leukemic cells are susceptible to the cytotoxic effects of the organic arsenic acid substituted compounds.

All publications, patents, and patent documents described herein are incorporated by reference as if fully set forth. The invention described herein may be modified to include alternative embodiments. All such obvious alternatives are within the spirit and scope of the invention, as claimed below.

We claim:
1. A compound of formula

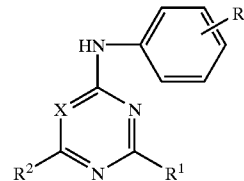

wherein R is

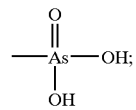

$R^1$ is hydrogen;
X is C;
$R^2$ is a group capable of bonding with X to form a fused substituted benzene, wherein the fused benzene ring is substituted by one or more groups selected from halo, hydroxy, $C_1$–$C_4$ alkoxy and trifluoromethyl; or a pharmaceutically acceptable salt thereof.

2. The compound of claim 1, wherein the fused benzene ring is substituted with two $C_1$–$C_4$ alkoxy groups.

3. A compound chosen from the group consisting of: 4-(2'-Phenyl arsenic acid)-amino-6,7-dimethoxyquinazoline, and 4-(4'-Phenyl arsenic acid)-amino-6,7-dimethoxyquinazoline.

4. A compound chosen from the group consisting of: 2-methylthio-4-(4'phenyl arsenic acid)-aminopyrimidine, and 2-methylthio-4-(2'-phenyl arsenic acid)-aminopyrimidine.

5. A pharmaceutical composition comprising a therapeutically effective amount of at least one compound chosen from the group consisting of: 2-methylthio4(4'phenyl arsenic acid)-aminopyrimidine, 2-methylthio4-(2'-phenyl arsenic acid)-aminopyrimidine, 4-(2'-Phenyl arsenic acid)-amino-6,7-dimethoxyquinazoline, and 4-(4'-Phenyl arsenic acid)-amino-6,7-dimethoxyquinazoline; and a pharmaceutically acceptable diluent or carrier.

6. A method for inhibiting the growth of tumor cells in a subject comprising administering to said subject a compound of the formula

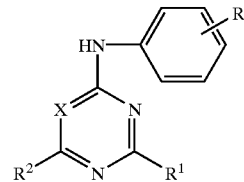

wherein R is

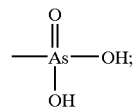

$R^1$ is H, $NR^3R^4$, $SR^3$, $OR^3$, in which $R^3$ and $R^4$ are each independently hydrogen or a $C_1$–$C_4$ alkyl group;
X is C;
$R^2$ is H, $NR^3R^4$, $SR^3$, $OR^3$, or a group capable of bonding with X to form a fused substituted or unsubstituted benzene or imidazole ring; or a pharmaceutically acceptable salt thereof.

7. The method of claim 6, wherein said inhibiting comprises inducing apoptosis in said tumor cells.

8. The method of claim 6 wherein the fused benzene ring is substituted by one or more groups selected from halo, hydroxy, mercapto, alkyl of 1–4 carbon atoms, alkoxy of 1–4 carbon atoms, thioalkyl of 1–4 carbon atoms, hydroxyalkyl of 1–4 carbon atoms, $NR^3R^4$, nitro, cyano, $CF_3$, COOH, $SO_3H$, and $SO_2NR^3R^4$ in which $R^3$ and $R^4$ are each independently hydrogen or a $C_1$–$C_4$ alkyl group.

9. The method of claim 8, wherein the fused benzene ring is substituted by one or more groups selected from halo, hydroxy, $C_1$–$C_4$ alkoxy and trifluoromethyl.

10. The method of claim 9, wherein the fused benzene ring is substituted with two $C_1$–$C_4$ alkoxy groups.

11. The method of claim 10, wherein the fused benzene ring is 3,4-dimethoxy benzene.

12. The method of claim 6, wherein $R^3$ is hydrogen or methyl, and $R^4$ is hydrogen.

13. The method of claim 6, wherein said compound is
4-(2'-Phenyl arsenic acid)-amino-6,7-dimethoxyquinazoline,
4-(4'-Phenyl arsenic acid)-amino-6,7-dimethoxyquinazoline,
2-Methylthio-4-(4'-phenyl arsenic acid)-aminopyrimidine, or
2-Methylthio-4-(2'-phenyl arsenic acid)-aminopyrimidine.

14. A method of treating cancer in a subject comprising administering to said subject a compound of the formula

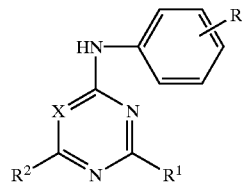

wherein R is

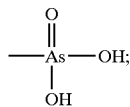

$R^1$ is H, $NR^3R^4$, $SR^3$, $OR^3$, in which $R^3$ and $R^4$ are each independently hydrogen or a $C_1$–$C_4$ alkyl group;
X is C;
$R^2$ is H, $NR^3R^4$, $SR^3$, $OR^3$, or a group capable of bonding with X to form a fused substituted or unsubstituted benzene or imidazole ring; or
a pharmaceutically acceptable salt thereof.

15. The method of claim 14, wherein said cancer is leukemia.

16. The method of claim 14, wherein said cancer is breast cancer.

17. The method of claim 14 wherein the fused benzene ring is substituted by one or more groups selected from halo, hydroxy, mercapto, alkyl of 1–4 carbon atoms, alkoxy of 1–4 carbon atoms, thioalkyl of 1–4 carbon atoms, hydroxyalkyl of 1–4 carbon atoms, $NR^3R^4$, nitro, cyano, $CF_3$, COOH, $SO_3H$, and $SO_2NR^3R^4$ in which $R^3$ and $R^4$ are each independently hydrogen or a $C_1$–$C_4$ alkyl group.

18. The method of claim 17, wherein the fused benzene ring is substituted by one or more groups selected from halo, hydroxy, $C_1$–$C_4$ alkoxy and trifluoromethyl.

19. The method of claim 18, wherein the fused benzene ring is substituted with two $C_1$–$C_4$ alkoxy groups.

20. The method of claim 19, wherein the fused benzene ring is 3,4-dimethoxy benzene.

21. The method of claim 14, wherein $R^3$ is hydrogen or methyl, and $R^4$ is hydrogen.

22. The method of claim 14, wherein said compound is
4,(2'-Phenyl arsenic acid)-amino-6,7-dimethoxyquinazoline,
4-(4'-Phenyl arsenic acid)-amino-6,7-dimethoxyquinazoline,
2-Methylthio-4-(4'-phenyl arsenic acid)-aminopyrimidine, or
2-Methylthio-4-(2'-phenyl arsenic acid)-aminopyrimidine.

23. A method for inducing cytotoxicity in a cell, comprising administering to said cell a cytotoxic dose of the compound of the formula

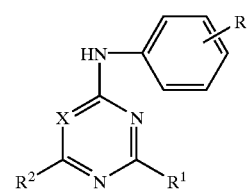

wherein R is

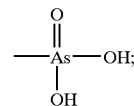

$R^1$ is H, $NR^3R^4$, $SR^3$, $OR^3$, in which $R^3$ and $R^4$ are each independently hydrogen or a $C_1$–$C_4$ alkyl group;
X is C;
$R^2$ is H, $NR^3R^4$, $SR^3$, $OR^3$, or a group capable of bonding with X to form a fused substituted or unsubstituted benzene or imidazole ring; or
a pharmaceutically acceptable salt thereof.

24. The method of claim 23, wherein said cell is a tumor cell.

25. The method of claim 23 wherein the fused benzene ring is substituted by one or more groups selected from halo, hydroxy, mercapto, alkyl of 1–4 carbon atoms, alkoxy of 1–4 carbon atoms, thioalkyl of 1–4 carbon atoms, hydroxyalkyl of 1–4 carbon atoms, $NR^3R^4$, nitro, cyano, $CF_3$, COOH, $SO_3H$, and $SO_2NR^3R^4$ in which $R^3$ and $R^4$ are independently hydrogen or a $C_1$–$C_4$ alkyl group.

26. The method of claim 25, wherein the fused benzene ring is substituted by one or more groups selected from halo, hydroxy, $C_1$–$C_4$ alkoxy and trifluoromethyl.

27. The method of claim 26, wherein the fused benzene ring is substituted with two $C_1$–$C_4$ alkoxy groups.

28. The method of claim 27, wherein the fused benzene ring is 3,4-dimethoxy benzene.

29. The method of claim 23, wherein $R^3$ is hydrogen or methyl, and $R^4$ is hydrogen.

30. The method of claim 23, wherein said compound is
4-(2'-Phenyl arsenic acid)-amino-6,7-dimethoxyquinazoline,
4-(4'-Phenyl arsenic acid)-amino-6,7-dimethoxyquinazoline,
2-Methylthio-4-(4'-phenyl arsenic acid)-aminopyrimidine, or
2-Methylthio-4-(2'-phenyl arsenic acid)-aminopyrimidine.

* * * * *

UNITED STATES PATENT AND TRADEMARK OFFICE
CERTIFICATE OF CORRECTION

PATENT NO. : 6,482,816 B1
DATED : November 19, 2002
INVENTOR(S) : Uckun et al.

It is certified that error appears in the above-identified patent and that said Letters Patent is hereby corrected as shown below:

<u>Title page,</u>
Item [56], References Cited, OTHER PUBLICATIONS, in the "Dai, J. et al.," reference, "by arsenic trioxide throught modulation" should read -- by arsenic trioxide through modulation --

<u>Column 4,</u>
Line 31, "[check formula]" should be deleted

<u>Column 10,</u>
Line 9, "tetrarethyl silane (TMS)," should read -- tetramethyl silane (TMS), --

<u>Column 13,</u>
Line 20, "(DMSO-$_6$):" should read -- (DMSO-$d_6$): --

<u>Column 14,</u>
Line 35, "Indianapolis, Id.)." should read -- Indianapolis, IN). --
Line 45, "WHI380, WMI381," should read -- WHI-P380, WHI-P381, --

<u>Column 15,</u>
Line 11, "Cytotolic" should read -- Cytotoxic --
Line 12, "leukemkic" should read -- leukemic --
Line 13, "(BT20) cells." should read -- (BT120) cells. --

<u>Column 20,</u>
Line 47, "$R^3$ and $R^4$ are independently" should read -- $R^3$ and $R^4$ are each independently --

Signed and Sealed this

Seventeenth Day of June, 2003

JAMES E. ROGAN
*Director of the United States Patent and Trademark Office*